(12) United States Patent
Abbate et al.

(10) Patent No.: US 8,277,498 B2
(45) Date of Patent: Oct. 2, 2012

(54) SYSTEM FOR DELIVERY OF A STENT AT AN ELEVATED TEMPERATURE

(75) Inventors: Anthony J. Abbate, Santa Clara, CA (US); Jeffrey David Royal, San Francisco, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 13/090,537

(22) Filed: Apr. 20, 2011

(65) Prior Publication Data

US 2011/0196471 A1    Aug. 11, 2011

Related U.S. Application Data

(62) Division of application No. 11/326,797, filed on Jan. 6, 2006, now Pat. No. 7,951,185.

(51) Int. Cl.
*A61F 2/06* (2006.01)

(52) U.S. Cl. .................. 623/1.11; 623/1.19

(58) Field of Classification Search ............ 623/1.1, 623/1.111, 1.19; 604/95.05, 103.01, 113, 604/96.01, 97.01, 98.01, 99.01; 606/27–31, 606/192–194

See application file for complete search history.

(56) References Cited

U.S. PATENT DOCUMENTS

| | | | |
|---|---|---|---|
| 2,392,199 A | 1/1946 | Steiger | |
| 4,754,752 A | 7/1988 | Ginsburg et al. | |
| 4,799,479 A | 1/1989 | Spears | |
| 5,129,915 A | 7/1992 | Cantenys | |
| 5,178,618 A | 1/1993 | Kandarpa | |
| 5,853,408 A | 12/1998 | Muni | |
| 5,957,962 A | 9/1999 | Wallsten et al. | |
| 5,992,419 A | 11/1999 | Sterzer et al. | |
| 6,613,082 B2 | 9/2003 | Yang | |
| 6,682,553 B1 | 1/2004 | Webler, Jr. | |
| 7,008,446 B1 | 3/2006 | Amis et al. | |
| 7,220,394 B2 | 5/2007 | Sreeram et al. | |
| 7,316,711 B2 | 1/2008 | Allen et al. | |
| 7,662,082 B2 | 2/2010 | White et al. | |
| 7,763,065 B2 | 7/2010 | Schmidt et al. | |
| 7,776,926 B1 | 8/2010 | Hossainy et al. | |
| 7,794,494 B2 | 9/2010 | Sahatjan et al. | |
| 7,951,185 B1 | 5/2011 | Abbate et al. | |
| 2003/0163190 A1 | 8/2003 | LaFont et al. | |
| 2004/0148014 A1 | 7/2004 | Nuutinen et al. | |
| 2004/0167600 A1 | 8/2004 | LaFont et al. | |
| 2004/0193179 A1 | 9/2004 | Nikolchev | |
| 2004/0267350 A1 | 12/2004 | Roubin et al. | |
| 2005/0010275 A1 | 1/2005 | Sahatjian et al. | |
| 2005/0049666 A1 | 3/2005 | Chien et al. | |

*Primary Examiner* — Dianne Dornbusch
(74) *Attorney, Agent, or Firm* — Squire Sanders (US) LLP

(57) ABSTRACT

Methods and systems of delivering a stent at an elevated temperature are disclosed herein.

9 Claims, 3 Drawing Sheets

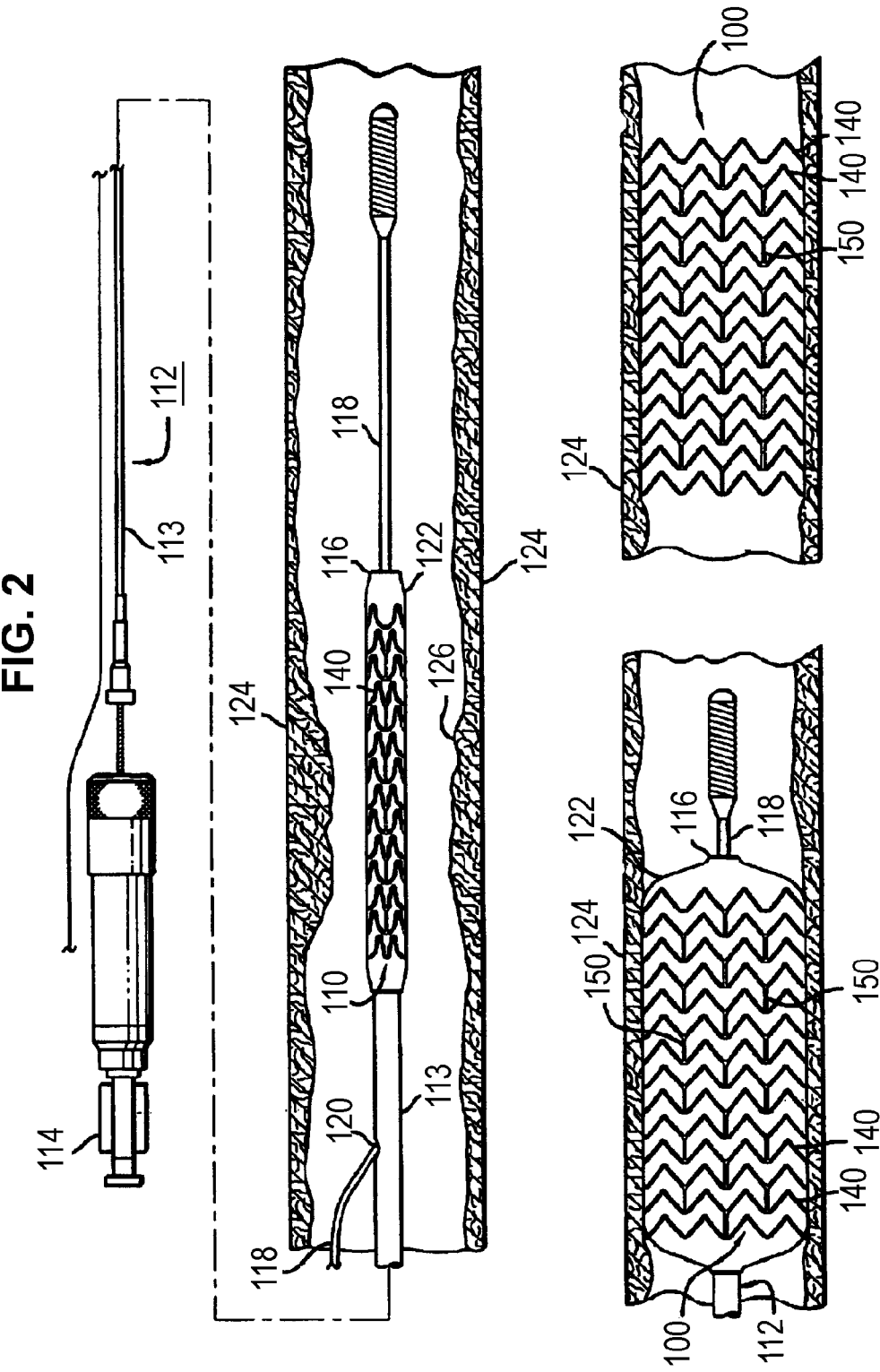

SYSTEM FOR DELIVERY OF A STENT AT AN ELEVATED TEMPERATURE

CROSS-REFERENCE TO RELATED APPLICATION

This application is a divisional of application Ser. No. 11/326,797, now U.S. Pat. No. 7,951,185, filed Jan. 6, 2006, which is incorporated herein by reference.

BACKGROUND OF THE INVENTION

1. Field of the Invention

This invention relates to methods and systems for delivery of polymeric stents.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

A potential problem with polymeric stents is that their struts or bar arms can crack during crimping and expansion. This is especially the case with brittle polymers. The localized portions of the stent pattern subjected to substantial deformation during crimping and expansion tend to be the most vulnerable to failure.

Another potential problem with polymeric stents is creep. Creep is a consequence of the viscoelastic nature of polymeric materials. Creep refers to the gradual deformation that occurs in a polymeric material subjected to an applied load. Creep occurs even when the applied load is constant. Creep in a polymeric stent reduces the effectiveness of a stent in maintaining a desired vascular patency. In particular, creep allows inward radial forces to permanently deform a stent radially inward.

Therefore, it is desirable for a stent to have flexibility and resistance to cracking during deployment. It is also advantageous for a stent to be rigid and resistant to creep after deployment.

SUMMARY OF THE INVENTION

Various embodiments of the present invention include a delivery system for delivering a stent at an implant site in a bodily lumen, comprising: a support member, the support member being coupled to a catheter in fluid communication with the support member; a stent crimped tightly over the support member; and a first reactant disposed within at least a portion of the support member, catheter, or both, the first reactant being disposed in such a way to react exothermically with a second reactant disposed within the delivery system, the heat generated from the exothermic reaction increasing a temperature of the stent mounted on the support member, and wherein the increase in temperature increases the flexibility of the stent such that formation of cracks in the stent upon its expansion is reduced or eliminated.

Further embodiments of the present invention include a delivery system for delivering a stent at an implant site in a bodily lumen, comprising: a catheter balloon coupled to a portion of a catheter in fluid communication with the balloon; a balloon expandable stent crimped tightly over the catheter balloon; and a solid coating including a first reactant and a second reactant on at least a portion of an interior surface of the balloon, wherein the first reactant and the second reactant react exothermically within the balloon upon exposure of the coating to a fluid.

Additional embodiments of the present invention include a delivery system for delivering a stent at an implant site in a bodily lumen, comprising: a catheter balloon coupled to a portion of a catheter in fluid communication with the balloon; a balloon expandable stent crimped tightly over the catheter balloon; and a solid coating including a first reactant on at least a portion of an interior surface of the balloon, a fluid including a second reactant; wherein the first reactant and the second reactant react exothermically within the balloon upon exposure of the coating to the fluid.

BRIEF DESCRIPTION OF THE DRAWINGS

FIG. 2 depicts an elevation view, partially in section, of a stent mounted on a delivery system.

FIG. 3 depicts an elevation view, partially in section, with a stent expanded within an artery.

FIG. 4 depicts an elevation view, partially in section, showing an expanded stent after withdrawal of a delivery catheter.

DETAILED DESCRIPTION OF THE INVENTION

Figure 1:
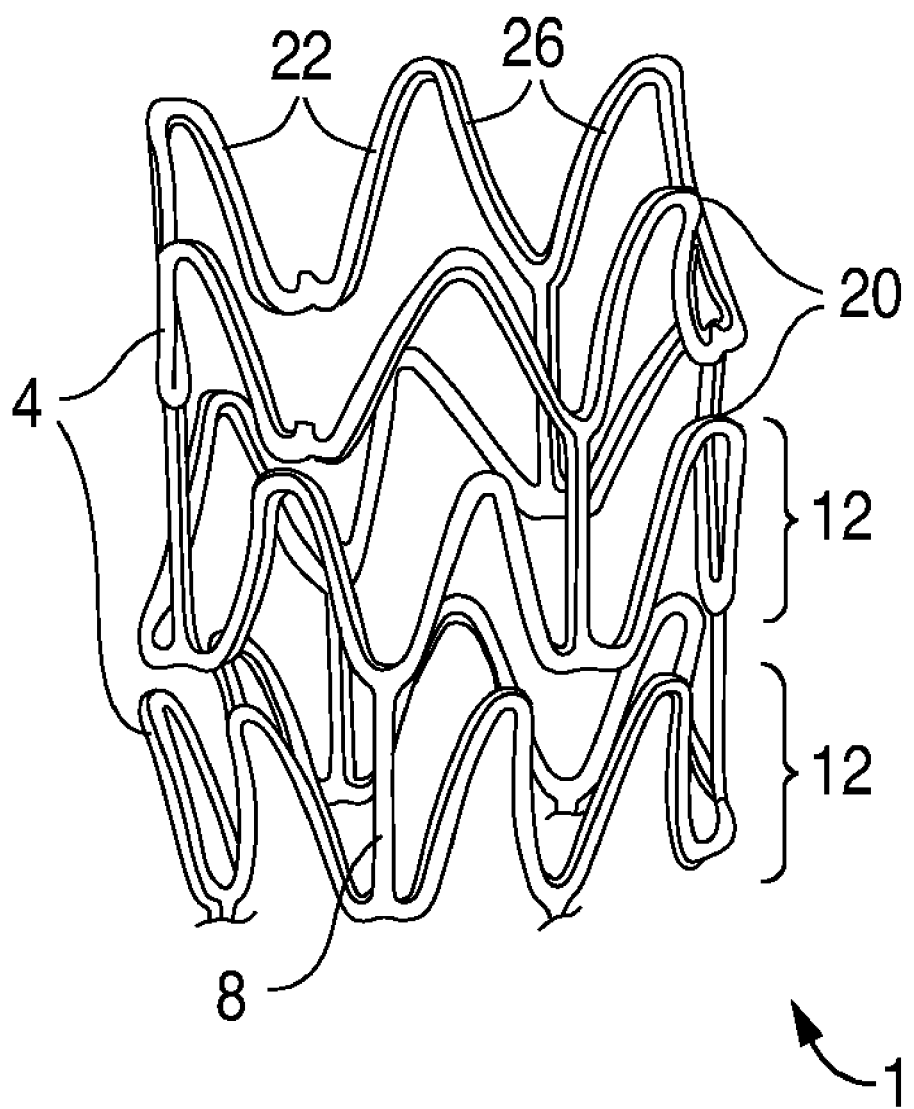
FIG. 1 depicts a stent.

Various embodiments of a method and system for delivery of stents are provided herein. In general, the embodiments relate to delivery of a stent at an elevated temperature. The elevated temperature increases the flexibility of the stent such that formation of cracks in the stent upon its expansion is reduced or eliminated. These embodiments may be applied in the delivery of balloon expandable and self-expandable stents. Embodiments of the method and system may also be applied to other implantable medical devices including, but not limited to, stent-grafts and grafts (e.g., aortic grafts).

Many treatment applications only require the presence of a stent in a bodily lumen for a limited period of time. To accommodate this, a stent can be made of a biodegradable polymer. A stent can also be made of a biostable or a combination of a biostable and biodegradable polymer. A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

Representative examples of polymers that may be used to fabricate or coat an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly (vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Implantable medical devices are typically subjected to stress during use, both before and during treatment. "Use" includes, but is not limited to, manufacturing, assembling (e.g., crimping stent on a catheter), delivery of a stent into and through a bodily lumen to a treatment site, and deployment of a stent at a treatment site. Both a scaffolding and a coating on a scaffolding experience stress that result in strain in the scaffolding and/or coating. For example, during deployment, the scaffolding of a stent can be exposed to stress caused by the radial expansion of the stent body. In addition, the scaffolding and/or coating may be exposed to stress when it is mounted on a catheter from crimping or compression of the stent.

Implantable medical devices, such as stents, that relate to the embodiments described herein typically include an underlying scaffolding or substrate. The underlying structure or substrate of the device can be of virtually any design. The substrate may have a polymer-based coating that may contain, for example, an active agent or drug for local administration at a diseased site. The active agent can be any substance capable of exerting a therapeutic or prophylactic effect.

FIG. 1 depicts a three-dimensional view of an exemplary embodiment of a cylindrically-shaped stent 1 with struts 4 that form cylindrical rings 12 which are connected by linking struts 8. The cross-section of the struts in stent 1 is rectangular-shaped. The struts have abluminal faces 20, luminal faces 22, and sidewall faces 26. The cross-section of struts is not limited to what has been illustrated, and therefore, other cross-sectional shapes are applicable with embodiments of the present invention. The pattern should not be limited to what has been illustrated as other stent patterns are easily applicable with embodiments of the present invention.

In general, a stent pattern is designed so that the stent can be radially compressed (crimped) and radially expanded (to allow deployment). The stresses involved during compression and expansion are generally distributed throughout various structural elements of the stent pattern. As a stent expands, various portions of the stent can deform to accomplish a radial expansion.

Additionally, fabrication of an implantable medical device, such as a stent, may include forming a pattern that includes a plurality of interconnecting structural elements or struts on a tube. Polymer tubes may be formed by various methods, including, but not limited to extrusion or injection molding. In some embodiments, the diameter of the polymer tube prior to fabrication of an implantable medical device may be between about 0.2 mm and about 5.0 mm, or more narrowly between about 1 mm and about 3 mm. In some embodiments, forming a pattern on a tube may include laser cutting a pattern on the tube. Representative examples of lasers that may be used include, but are not limited to, excimer, carbon dioxide, and YAG. In other embodiments, chemical etching may be used to form a pattern on a tube.

FIGS. 2-4 illustrate an exemplary delivery system for delivering a balloon expandable stent. FIG. 2 depicts a stent 100 with interconnected cylindrical rings 140 mounted on a catheter assembly 112 which is used to deliver stent 100 and implant it in a bodily lumen. Rings 140 are connected by links 150.

For example, a bodily lumen may include a coronary artery, peripheral artery, or other vessel or lumen within the body. The catheter assembly includes a catheter shaft 113 which has a proximal end 114 and a distal end 116. The catheter assembly is configured to advance through a vascular system over a guide wire by any of the well-known methods of an over-the-wire system (not shown) or a well-known rapid exchange catheter system, such as the one shown in FIG. 2. Stent 100 in FIGS. 2-4 conceptually represents any type of stent well-known in the art, i.e., one having a plurality of rings 140.

Catheter assembly 112, as depicted in FIG. 2, includes a port 120 where guide wire 118 exits the catheter. The distal end of guide wire 118 exits catheter distal end 116 so that the catheter advances along the guide wire on a section of the catheter between port 120 and catheter distal end 116. As is known in the art, the guide wire lumen which receives the guide wire is sized for receiving various diameter guide wires to suit a particular application. The stent is mounted on an expandable member 122 (e.g., a balloon) and is crimped tightly thereon, so that the stent and expandable member present a low profile diameter for delivery through the arteries.

As shown in FIG. 2, a partial cross-section of an artery 124 has a small amount of plaque that has been previously treated by angioplasty or other repair procedure. Stent 100 can be used to repair a diseased or damaged arterial wall as shown in FIG. 2, or a dissection, or a flap, all of which are commonly found in the coronary arteries and other vessels. Stent 100, and other embodiments of stents, also can be placed and implanted without any prior angioplasty.

In a typical procedure to implant stent 100, guide wire 118 is advanced through the vascular system by well-known methods, so that the distal end of the guide wire is advanced past the plaque or a diseased area 126. Prior to implanting the stent, the cardiologist may wish to perform an angioplasty or other procedure (i.e., atherectomy) in order to open and remodel the vessel and the diseased area. Thereafter, stent delivery catheter assembly 112 is advanced over the guide wire so that the stent is positioned in the implant area or site.

The expandable member or balloon 122 is inflated by injecting a fluid into proximal end 114 of the catheter. Balloon 122 expands radially outwardly and in turn expands the stent radially outwardly until the stent is apposed to the vessel wall. Expandable member 122 is then deflated and the catheter withdrawn from the patient's vascular system.

The guide wire typically is left in the lumen for post-dilatation procedures, if any, and subsequently is withdrawn from the vascular system. As depicted in FIGS. 3 and 4, the balloon is fully inflated with the stent expanded and pressed against the vessel wall. In FIG. 4, the implanted stent remains in the vessel after the balloon has been deflated and the catheter assembly and guide wire have been withdrawn from the patient. Stent 100 holds open the artery after the catheter is withdrawn, as illustrated by FIG. 4.

In the case of a self-expandable stent, constraining members such as sheaths may be used to secure a self-expanding stent to a catheter. The stent, constrained or secured by the sheath, is positioned at a desired treatment location. The sheath is then withdrawn which allows the stent to self-expand. Expansion is typically spontaneous. Additionally, a sheath may also be used when delivering a balloon-expandable stent. In this case, a sheath inhibits or prevents detachment of the crimped stent from the catheter prior to deployment of the crimped stent at an implant site.

As indicated above, the structural members of polymeric stents can crack during crimping and radial expansion. This can lead to mechanical failure of stent after deployment. Such cracking or rupturing can cause a stent strut to dislodge. The dislodged stent can cause an embolism in the lumen of the tubular organ. In addition, a dislodged stent can orient itself perpendicular to blood flow thereby causing thrombosis.

Rigid polymers are particularly susceptible to cracking when deformed such as when a stent is radially expanded. Polymers below their glass transition temperature tend to be rigid. The "glass transition temperature," $T_g$, is the temperature at which the amorphous domains of a polymer change from a brittle vitreous state to a solid deformable or ductile state at atmospheric pressure. In other words, the $T_g$ corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. $T_g$ of a given polymer can be dependent on the heating rate and can be influenced by the thermal history of the polymer. Furthermore, the chemical structure of the polymer heavily influences the glass transition by affecting mobility.

Below the $T_g$ of a polymer, polymer segments may not have sufficient energy to move past one another. A polymer in a rigid state may be better suited to resist radial compressive forces in a stent once a stent is deployed. Thus, it would be advantageous for the polymer of a stent to have a $T_g$ that is above body temperature. However, such a polymer when it is below its $T_g$ is susceptible to embrittlement and cracking during radial expansion.

As the temperature of a polymer is increased close to or above $T_g$, the energy barriers to rotation decrease and segmental mobility of polymer chains tends to increase. Consequently, polymers become more flexible, and thus, more resistant to embrittlement and cracking when they are at a temperature that is close to or above $T_g$. Therefore, it may be more desirable for a polymeric stent to be close to or above the $T_g$ of the polymer when a stent is expanded.

However, polymers tend to be more susceptible to creep when they are close to or above the $T_g$. Additionally, creep can also result in a polymeric stent under stress. In particular, creep allows inward radial forces to permanently deform a stent radially inward. Therefore, creep reduces the effectiveness of a stent in maintaining a desired vascular patency.

In general, it is desirable to have a delivery system that allows a stent to be (1) flexible and resistant to cracking during expansion (2) rigid and resistant to compressive forces so as to maintain vascular patency after deployment at an implant site.

Various embodiments of a method and system for delivering a stent in a bodily lumen that meet these criteria are disclosed. In general, the criteria may be met in part by using a stent fabricated from a polymer that is rigid at body temperature, e.g., a polymer with a $T_g$ greater than body temperature. The other criterion may be met by increasing the flexibility of the stent during expansion such that formation of cracks in the stent upon its expansion is reduced or eliminated. This may be accomplished by heating a stent to a temperature close to, at, or above its $T_g$.

In certain embodiments, a delivery system for delivering a stent at an implant site in a bodily lumen may include a support member for supporting the stent and a catheter in fluid communication with the support member. The support member may be an expandable member such as a catheter balloon, as described above. Alternatively, in the case of a self-expanding stent, the supporting member may be a portion of a catheter.

In certain embodiments, a method of delivering a stent mounted on a support member of the delivery system may include allowing a first reactant and a second reactant to react within the delivery system. The method may include disposing the first reactant and the second reactant within a portion of the delivery system to react. In one embodiment, the first reactant and the second reactant may be combined in a fluid to allow the reaction followed by disposing the fluid into the delivery system.

In an embodiment, the first and second reactants may react in a fluid within the support member, a catheter in fluid communication with the support member, or both. The first and the second reactants may react exothermically. The method may further include allowing heat generated from the exothermic reaction to increase a temperature of the stent mounted on the support member. The method may also include allowing the stent to cool after the stent is expanded and the reaction no longer heats the stent.

Moreover, the reaction may include one or more additional reactants. In an embodiment, the additional reactants may be disposed in the delivery system to allow the reaction to occur. In addition, the reaction may be facilitated by the presence of a catalyst. A "catalyst" refers to a substance that increases the rate of a chemical reaction by reducing the activation energy, but which is left unchanged by the reaction. The method may include disposing the catalyst in the delivery system.

Representative reactants that may be used include, but are not limited to water ($H_2O$) and sodium peroxide ($Na_2O_2$); glycerin and potassium nitrate ($KNO_3$); and sulfur and sugar.

In an embodiment, the increase in temperature may increase the flexibility of the stent such that formation of cracks in the stent upon its expansion is reduced or eliminated. The heat from the reaction may increase a temperature of the stent close to, at, or above a glass transition temperature of the polymer of the stent.

As indicated above, the support member may be an expandable member for expanding a balloon-expandable stent. Thus, one embodiment of the method may further include expanding the stent by inflating the expandable member. After expansion of the stent, the balloon may be deflated and removed from the implant site. In some embodiments, the stent may be allowed to heat set for a period of time by keeping the balloon inflated. "Heat setting" refers to the equilibration of polymer chains at an elevated temperature. In the case of a self-expandable stent, another embodiment of the method may further include allowing the stent to self-expand.

Additionally, reactants may be disposed in a solid or fluid phase. One or more of the reactants may be a liquid or dissolved in a solvent. Fluids may be injected into the catheter and support member from the proximal end of the catheter, e.g., see FIG. 2.

Reactants disposed in a solid phase may be particles that include one or more of the reactants. Particles may be disposed in the support member, catheter, or both prior to positioning the support member at the implant site. For example, particles may be disposed in the support member at the time of fabrication of the delivery system. Also, particles may be suspended in a fluid which can be injected into the catheter and support member. The reactant in the particles may be capable of being dissolved by the fluid so that the reaction may occur in the fluid phase.

Alternatively, the support member may include a coating on at least a portion of an interior surface of the catheter, the support member, or both. The coating may include at least one of the reactants. In one embodiment, the coating may be composed completely or substantially of one or more of the reactants. In another embodiment, the coating may include a mixture of one or more reactants and nonreactive material. A coating may be applied to an interior surface of the balloon using any commonly known method such as spraying or dipping. Coating material may be applied as a mixture of a solvent, one or more reactants, and nonreactive material. All or substantially all of the solvent may then be removed to form the coating.

Furthermore, reactants may be allowed to react in several ways. In one embodiment, a fluid including the first and second reactants may be disposed into the delivery system. The fluid may include the first and the second reactants. Alternatively, the fluid may include the first reactant. Another fluid including the second reactant may be disposed at the same time or after the fluid including the first reactant to allow the reaction of the reactants.

In another embodiment, particles including the first reactant may be disposed within the support member, catheter, or both. A fluid including the second reactant may be disposed into the delivery system to react with the first reactant. At least a portion of the first reactant may be dissolved by the fluid and react with the second reactant in the fluid phase. In some embodiments, at least a portion of the second reactant may diffuse into the particles and react with the first reactant. In an additional embodiment, the injected fluid may have suspended particles that include the second reactant for reacting with the first reactant.

In other embodiments, the catheter, support member, or both may contain particles including both the first and second reactants. Individual particles may have one or both of the reactants. The reactants may react upon exposure of the particles to a fluid injected into the catheter and support member.

In further embodiments, particles with the first reactant suspended in a fluid may be injected into a catheter and support member. Particles with the second reactant suspended in a fluid may then be injected to initiate the reaction.

In an additional embodiment, a fluid including the second reactant may be disposed within the delivery system to react with the first reactant included in a coating. The coating may be above at least a portion of an interior surface of the support member, an interior surface of a catheter in fluid communication with the support member, or both. The first reactant in the coating may be dissolved by the fluid so that first reactant can react with the second reactant in the fluid phase.

Additionally, a coating may include the first reactant and the second reactant. The reactants may react upon exposure of the coating to a fluid disposed into the delivery system.

In addition, the reaction may be initiated at selected times during the delivery. Embodiments may include positioning the mounted stent with the delivery system at an implant site before, during, and/or after allowing the first reactant and the second reactant to react.

In some embodiments, the method may further include mixing a fluid within the delivery system including the first reactant and second reactant to facilitate the reaction. A mixing device may be within or coupled to the support member, catheter, or both. Alternatively, the flow of fluid in the delivery system may be sufficient to mix the fluid to allow the reaction.

Additionally, the increase in temperature can be controlled by, for example, selecting reactants with a particular heat of reaction and the amount of reactants disposed within the delivery system. A reaction with a higher heat of reaction and a greater amount of reactants in the delivery system tends to result in a higher increase in temperature.

Also, it may be desirable to control the duration of heating of the stent. In one embodiment, the duration may be controlled by increasing or decreasing the amount of reactants in the delivery system. For example, the amount of coating material on the interior surface of the balloon or catheter may be altered to control the amount and duration of the heating of the stent. The duration and amount of heat may also be controlled by altering the amount nonreactive material in the coating. For example, increasing the amount of nonreactive material may increase the duration of heating as well as decrease the rate of heating of the stent.

It may be desirable to have a relatively high rate of heating and/or heat of reaction so that the stent can be heated relatively quickly to increase the flexibility during the expansion process. In one embodiment, a balloon may be partially expanded prior to disposing a fluid into the balloon which initiates the reaction. The stent may be allowed to increase in temperature from the heat of the reaction prior to further expansion. After a period of time, during which the temperature of the stent in increased, the stent can be further expanded.

In addition, the duration of a reaction may be controlled by limiting the amount of reactant in a fluid, a coating, or particle. The reaction will terminate once one of the reactants is consumed.

Figure 5:
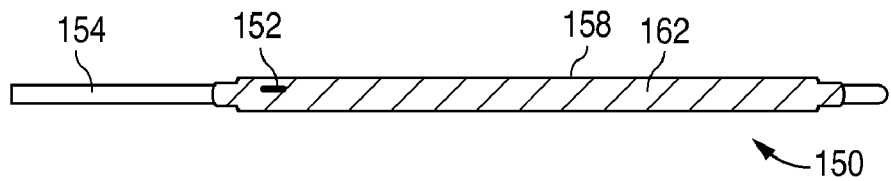
FIG. 5 depicts a portion of an axial cross-section of a delivery system with a balloon having a coating on an interior surface.

FIG. 5 depicts a portion of an axial cross-section of a delivery system 150 that includes a catheter 154 in fluid communication with an expandable member or balloon 158 with a lumen port 152. Balloon 158 is shown in a crimped or deflated state. A stent (not shown) can be mounted on balloon 158 as illustrated in FIGS. 2-3. An interior surface of balloon 158 has a coating 162 that includes a first reactant.

Figure 6:
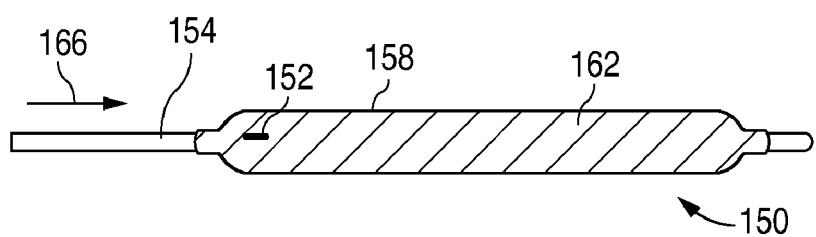
FIG. 6 depicts the delivery system of FIG. 5 with the balloon inflated.
Figure 7:
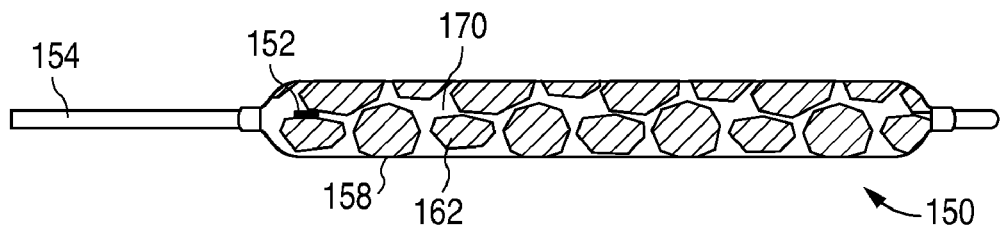
FIG. 7 depicts the delivery system of FIG. 5 with the balloon fully inflated.

FIG. 6 depicts delivery system 150 as balloon 158 is inflated. A fluid containing a second reactant is injected into and flows through catheter 154 as shown by an arrow 166. Fluid fills balloon 158 causing balloon 158 to inflate. The first reactant in the coating and the second reactant in the fluid react as fluid enters balloon 158 and inflates the balloon. A stent (not shown) mounted on the balloon is heated by the heat generated by the exothermic reaction. FIG. 7 depicts delivery system 150 with balloon 158 fully inflated. Coating 162 has been partially consumed by the reaction as shown by depleted portions 170.

Figure 8:
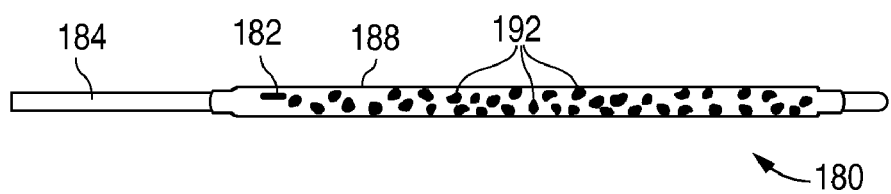
FIG. 8 depicts a portion of an axial cross-section of a delivery system with a balloon having particles disposed within.

FIG. 8 depicts a portion of an axial cross-section of a delivery system 180 that includes a catheter 184 in fluid communication with an expandable member or balloon 188 with a lumen port 182. As in FIG. 5, balloon 158 is shown in a crimped or deflated state. Particles 162 including a first reactant are disposed within balloon 158.

Figure 9:
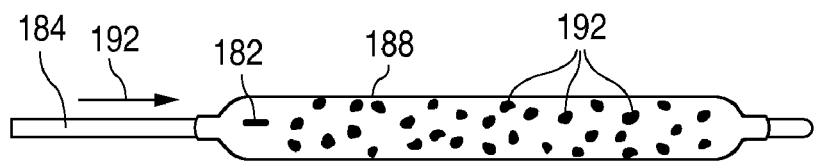
FIG. 9 depicts the delivery system of FIG. 8 with the balloon inflated.

FIG. 9 depicts delivery system 180 as balloon 188 is inflated. A fluid flows through catheter 184 as shown by an arrow 192. Fluid fills balloon 188 causing balloon 188 to inflate. The first reactant in the particles and the second reactant in the fluid react as fluid enters balloon 188 and inflates the balloon. As described before, a stent (not shown) mounted on the balloon is heated by the heat generated by the exothermic reaction.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

The invention claimed is:

1. A delivery system for delivering a stent at an implant site in a bodily lumen, comprising:

a balloon coupled to a catheter in fluid communication with the balloon;

a stent crimped tightly over the balloon, wherein the balloon is in a deflated state prior to injection of an inflation fluid; and a first reactant disposed within at least a portion of the balloon in the deflated state, the first reactant being disposed in such away to react exothermically with a second reactant when the balloon is inflated, the heat generated from the exothermic reaction increasing a temperature of the stent mounted on the support member, and wherein the increase in temperature increases the flexibility of the stent such that formation of cracks in the stent upon its expansion is reduced or eliminated.

2. The system of claim 1, wherein the stent comprises a biostable and/or bioabsorbable polymer.

3. The system of claim 1, wherein the first reactant is included in a coating on at least a portion of an interior surface of the balloon in the deflated state.

4. The system of claim 3, wherein the coating comprises the second reactant, wherein the first and second reactants react when the coating is exposed to a fluid.

5. A delivery system for delivering a stent at an implant site in a bodily lumen, comprising:

a catheter balloon coupled to a portion of a catheter in fluid communication with the balloon;

a balloon expandable stent crimped tightly over the catheter balloon; and a solid coating including a first reactant on at least a portion of an interior surface of the balloon, wherein the first reactant and a second reactant react exothermically within the balloon upon exposure of the coating to a fluid including the second reactant.

6. The system of claim 5, wherein the stent comprises a scaffolding including a plurality of interconnecting structural elements.

7. The system of claim 5, wherein the stent is made of a biodegradable polymer.

8. The system of claim 7, wherein the biodegradable polymer has a glass transition temperature greater than body temperature.

9. The system of claim 7, wherein the biodegradable polymer is poly(L-lactide).

* * * * *